United States Patent
Kardorff et al.

[11] Patent Number: 5,082,852
[45] Date of Patent: Jan. 21, 1992

[54] CYCLOPROPANECARBOXAMIDES AND THEIR USE FOR CONTROLLING PESTS

[75] Inventors: Uwe Kardorff, Mannheim; Hans-Juergen Neubauer, Muenster-Hiltrup; Joachim Leyendecker, Ladenburg; Christoph Kuenast, Otterstadt; Peter Hofmeister, Neustadt; Wolfgang Krieg, Weingarten, all of Fed. Rep. of Germany

[73] Assignee: BASF Aktiengesellschaft, Ludwigshafen, Fed. Rep. of Germany

[21] Appl. No.: 568,547

[22] Filed: Aug. 15, 1990

Related U.S. Application Data

[63] Continuation of Ser. No. 376,768, Jul. 7, 1989, abandoned.

[30] Foreign Application Priority Data

Jul. 21, 1988 [DE] Fed. Rep. of Germany ....... 3824788

[51] Int. Cl.$^5$ .......................................... A01N 43/40
[52] U.S. Cl. ................................. 514/351; 514/247; 514/255; 514/269; 544/239; 544/298; 544/408
[58] Field of Search .................. 514/351; 546/300

[56] References Cited

U.S. PATENT DOCUMENTS

| | | | |
|---|---|---|---|
| 4,565,822 | 1/1986 | Tessler | 546/300 |
| 4,796,773 | 12/1990 | Fukami | 546/300 |
| 4,798,839 | 1/1989 | Ayao | 574/351 |
| 4,822,806 | 4/1989 | Ackermann | 546/300 |
| 4,849,450 | 7/1989 | Holan et al. | 546/300 |

*Primary Examiner*—Donald G. Daus
*Attorney, Agent, or Firm*—Oblon, Spivak, McClelland, Maier & Neustadt

[57] ABSTRACT

Cyclopropanecarboxamides of the general formula I

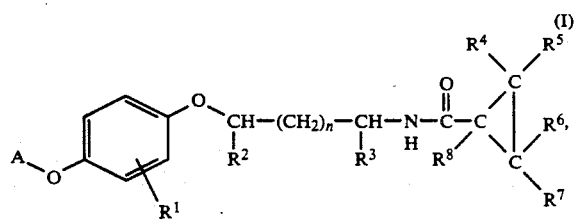

wherein $R^1$ is hydrogen, halogen or low-molecular-weight alkyl, $R^2$ and $R^3$ are hydrogen or low-molecular-weight alkyl, $R^4$ to $R^8$ are each hydrogen, halogen or low-molecular-weight alkyl, A is substituted or unsubstituted hetaryl with 1, 2 or 3 nitrogen atoms and six ring members, n is 0 or 1, methods for their manufacture, and their use for combating pests.

15 Claims, No Drawings

CYCLOPROPANECARBOXAMIDES AND THEIR USE FOR CONTROLLING PESTS

This application is a continuation of application Ser. No. 07/376,768, filed on July 7, 1989, now abandoned.

The present invention relates to novel cyclopropanecarboxamides of the general formula I

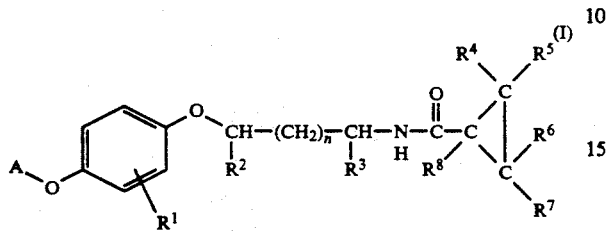

where $R^1$ and $R^4$-$R^8$ are each hydrogen, halogen or low molecular weight alkyl, $R^2$ and $R^3$ are each hydrogen or low molecular weight alkyl, A is unsubstituted or substituted hetaryl having 1, 2 or 3 nitrogen atoms and six ring members and n is 0 or 1.

The present invention furthermore relates to the preparation of the compounds I, pesticides which contain the compounds I and a method for controlling pests.

DE-A 33 20 534 discloses the carbamic ester A

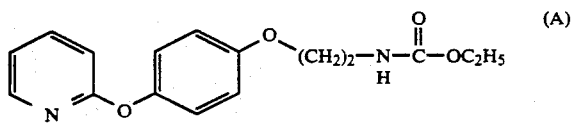

and DE-A 36 28 082 discloses the cyclopropanecarboxamide B

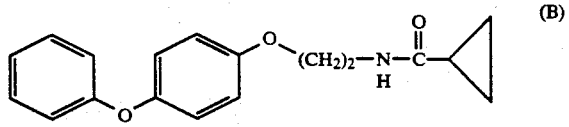

as pesticides.

However, the action, application rate and/or outdoor stability of the compounds A and B are not always satisfactory.

It is an object of the present invention to provide novel cyclopropanecarboxamides I having an improved action and/or compounds I which are more effective against other pests.

We have found that this object is achieved by the novel cyclopropanecarboxamides I defined at the outset and processes for their preparation. We have also found that the compounds I are very suitable as pesticides.

The compounds I are obtainable by reacting a primary amine of the general formula II

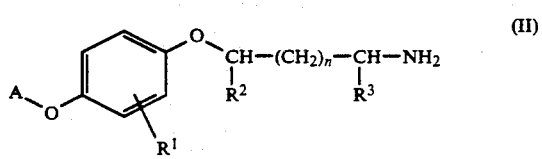

with a cyclopropanecarbonyl halide of the general formula III

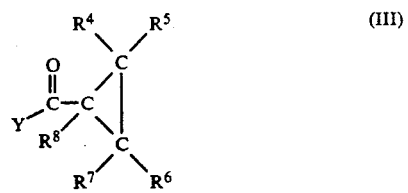

where Y is halogen, in the presence of an acid acceptor.

The amine II can be used as the acid acceptor. As a rule, however, a conventional acid acceptor, such as an aliphatic, aromatic or heterocyclic amine, e.g. triethylamine, dimethylamine, diisopropylamine, piperidine, dimethylaniline, dimethylbenzylamine, pyridine or 4-dimethylaminopyridine, a hydroxide of an alkali metal or an alkaline earth metal, e.g. sodium hydroxide, potassium hydroxide or calcium hydroxide, an alcoholate of an alkali metal or of an alkaline earth metal, e.g. sodium methylate, sodium ethylate, calcium methanolate or potassium tert-butylate, an alkali metal hydride or alkaline earth metal hydride, e.g. sodium hydride, potassium hydride or calcium hydride, or an alkali metal carbonate or alkaline earth metal carbonate, e.g. sodium carbonate, potassium carbonate or calcium carbonate, is used.

The reactions are advantageously carried out in a solvent or diluent. Aliphatic or aromatic hydrocarbons or chlorohydrocarbons, such as petroleum ether, n-pentane, n-hexane, hexane isomer mixtures, benzene, toluene, xylene, gasoline, dichloromethane, chloroform, carbon tetrachloride, 1,2-dichloroethane and chlorobenzene, ethers and esters, such as diethyl ether, di-n-butyl ether, methyl tert-butyl ether, tetrahydrofuran, dioxane and ethyl acetate, ketones, such as acetone, methyl ethyl ketone or methyl isopropyl ketone, nitriles, such as acetonitrile or propionitrile, alcohols, such as methanol, ethanol, n-propanol or isopropanol, and aprotic dipolar solvents, such as dimethylformamide, dimethyl sulfoxide and pyridine, are suitable for this purpose. Mixtures of these substances can also be used as solvents and diluents.

Usually, the starting materials II and III are used in an equimolar ratio, but an excess of one or other of the components may be quite advantageous in specific cases. The amount of base is in general from 0.5 to 20, preferably from 0.7 to 5, particularly preferably from 0.9 to 1.5, moles per mole of acyl halide III.

The reaction can be carried out at from $-30°$ to $120°$ C., preferably from $-10°$ to $80°$ C., particularly preferably from $0°$ to $50°$ C., under atmospheric, superatmospheric or reduced pressure, by a conventional method.

Some of the primary amines II used for the preparation of the compounds I are known from the literature and can be prepared by corresponding methods, which are described in Houben-Weyl, Vol. VI, 3, Methoden der organischen Chemie, Thieme Verlag, 1965, 85 et seq.

The acyl halides, in particular acyl bromides and acyl chlorides III, which are also required are known or are obtainable in a conventional manner, and some of them are commercially available.

The novel compounds of the formula I can also be prepared by virtually any known process of carboxamide synthesis, for example by reacting an appropriate primary amine II with an appropriate cyclopropanecarboxylate, cyclopropanecarboxylic acid or one of its salts, cyclopropanecarboxylic anhydride or ketene derivative (cf. C. Ferri, Reaktionen der organischen Synthese, Georg Thieme Verlag, Stuttgart, 1978, page 542, and the literature cited there).

Some of the novel compounds of the formula I are obtained in the form of colorless or pale brown oils, which can be freed from the final volatile constituents by prolonged heating under reduced pressure to moderately elevated temperatures (incipient distillation) and can be purified in this manner. If the compounds of the formula I are obtained in crystalline form, they may be purified by recrystallization.

In the compounds of the formula I, $R^1$ is preferably hydrogen, halogen, such as fluorine, chlorine or bromine, preferably fluorine or chlorine, or straight-chain or branched $C_1$-$C_3$-alkyl, such as methyl, ethyl or isopropyl, $R^2$ and $R^3$ are identical or different and are each preferably hydrogen, straight-chain or branched $C_1$-$C_4$-alkyl, such as methyl, ethyl, propyl, isopropyl, butyl or a butyl isomer, preferably methyl or ethyl, or branched alkyl such as isopropyl, isobutyl or sec-butyl, $R^4$-$R^8$ are identical or different and are each preferably hydrogen, halogen, such as fluorine, chlorine or bromine, preferably fluorine or chlorine, or straight-chain or branched $C_1$-$C_4$-alkyl, such as methyl, ethyl, propyl, isopropyl or butyl, preferably methyl, ethyl or isopropyl, A is a nitrogen-containing hetaryl radical, unsubstituted or substituted by $R^9$ and having six ring members, of the general formulae IV.1-IV.5

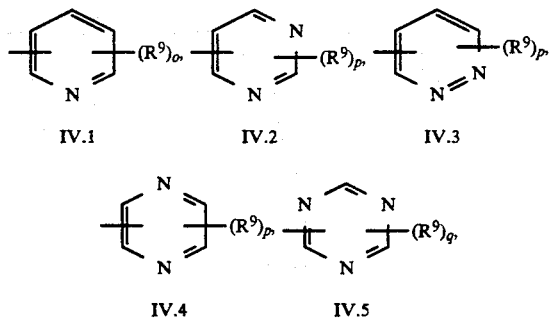

where O is from 1 to 4, p is from 1 to 3 and q is 1 or 2, and $R^9$ is hydrogen, halogen, such as fluorine, chlorine or bromine, preferably fluorine or chlorine, straight-chain or branched $C_1$-$C_4$-alkyl, such as methyl, ethyl, propyl or butyl, preferably methyl or ethyl, or branched alkyl such as isopropyl, isobutyl, sec-butyl, straight-chain or branched $C_1$-$C_3$-haloalkyl, preferably fluoro- or chloroalkyl, such as fluoromethyl, difluoromethyl, trifluoromethyl, pentafluoroethyl, 2,2,2-trifluoroethyl, trichloromethyl or 2,2,2-trichloroethyl, straight-chain or branched $C_1$-$C_4$-alkoxy, such as methoxy, ethoxy, propoxy or butoxy, preferably methoxy, ethoxy or isopropoxy, straight-chain or branched $C_1$-$C_3$-haloalkoxy, preferably fluoro- or chloroalkoxy, such as trifluoromethoxy, 1,1,2,2-tetrafluoroethoxy, pentafluoroethoxy and trichloromethoxy, $C_3$-$C_6$-cycloalkyl, such as cyclopropyl, cyclobutyl, cyclopentyl or cyclohexyl, preferably cyclopropyl, cyano or nitro, and, where o, p or q is $> 1$, the radicals $R^9$ may be identical or different.

Particularly preferred hetaryl radicals are pyrid-2-yl, pyrid-3-yl, pyrid-4-yl, pyrimidin-2-yl, pyrimidin-4-yl, pyrimidin-5-yl, pyridazin-3-yl, pyridazin-4-yl, pyrazin-2-yl, pyrazin-3-yl and s-triazin-2-yl, particularly preferably pyrid-2-yl, pyrimidin-2-yl, pyrimidin-4-yl, pyrimidin-5-yl, pyridazin-3-yl and pyrazin-3-yl.

The novel compounds I may contain one or more centers of asymmetry. The present invention embraces all possible stereoisomers, such as diastereomers, enantiomers and all possible diastereomer and enantiomer mixtures.

The cyclopropanecarboxamides of the formula I are suitable for effectively combating pests from the class of insects, mites and nematodes. They may be used as pesticides in crop protection, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are *Blitophaga undata, Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla*

*mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are *Reticulitermes lucifugus, Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Stauronotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are rootknot nematodes, e.g., *Meloidogyne incognita, Meloidogyne hapla,* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Examples of formulations are given below.

I. 5 parts by weight of compound no. 1 is intimately mixed with 95 parts by weight of particulate kaolin. A dust is obtained containing 5% by weight of the active ingredient.

II. 30 parts by weight of compound no. 6 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. 6 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. 1 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. 1 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredient applied is for example from 0.01 to 10, particularly from 0.05 to 2, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

MANUFACTURING EXAMPLE

Example 1

N-{2-[4-(6-chloropyridin-2-yloxy)-phenoxy]-eth-1-yl}-cyclopropanecarboxamide

At room temperature, 1.1 g of triethylamine and then 1.0 g of cyclopropanecarboxylic acid chloride are dripped into 2.6 g of 2-[4-(6-chloropyridin-2-yloxy)-phenoxy]-ethylamine in 50 cm$^3$ of dichloromethane. The reaction is slightly exothermic. The mixture is stirred at room temperature for 14 hours.

It is then poured onto ice water and extracted with dichloromethane. The combined organic phases are dried over sodium sulfate and concentrated in a rotary evaporator. A white solid remains; melting range 114°–117° C.

Yield: 1.0 g $\hat{=}$ 30.6% of theory.

The following compounds I listed in Table 1 below may be prepared analogously. Where the substances are not crystalline, the infrared absorption maxima in the range below about 1500 cm$^{-1}$ are given.

TABLE 1

Cyclopropanecarboxamides

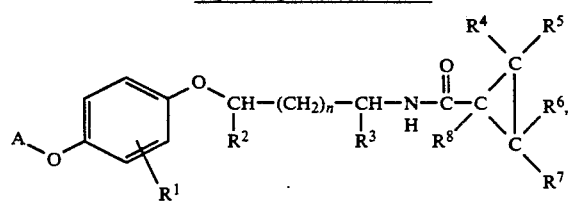

(I)

| Ex. No. | A | A attached in the ...-position | $R^1$ | $R^2$ | $R^3$ | $R^4$ | $R^5$ | $R^6$ | $R^7$ | $R^8$ | n | m.p. (°C.) or IR data (cm$^{-1}$) |
|---|---|---|---|---|---|---|---|---|---|---|---|---|
| 1 | 2-chloropyridinyl | 2 | H | H | H | H | H | H | H | H | 0 | 114–117 |
| 2 | 2-chloropyridinyl | 2 | H | CH$_3$ | H | H | H | H | H | H | 0 | |
| 3 | 2-chloropyridinyl | 2 | H | H | H | CH$_3$ | H | H | H | H | 0 | |
| 4 | 2-fluoropyridinyl | 2 | H | H | H | H | H | H | H | H | 0 | 74–77 |
| 5 | 2-trifluoromethylpyridinyl | 2 | H | H | H | CH$_3$ | H | H | H | H | 0 | |
| 6 | 2-trifluoromethylpyridinyl | 2 | H | H | H | H | H | H | H | H | 0 | 116–118 |

TABLE 1-continued

Cyclopropanecarboxamides $$A-O-\underset{R^1}{\underset{|}{\bigcirc}}-O-\underset{R^2}{\underset{|}{CH}}-(CH_2)_n-\underset{R^3}{\underset{|}{CH}}-\underset{H}{\underset{|}{N}}-\underset{\|}{\overset{O}{C}}-\underset{R^8}{\overset{R^4}{\underset{|}{C}}}\underset{R^7}{\overset{R^5}{\underset{|}{\underset{C}{\overset{|}{C}}}}}R^6,\qquad (I)$$

| Ex. No. | A | A attached in the ...-position | $R^1$ | $R^2$ | $R^3$ | $R^4$ | $R^5$ | $R^6$ | $R^7$ | $R^8$ | n | m.p. (°C.) or IR data (cm$^{-1}$) |
|---|---|---|---|---|---|---|---|---|---|---|---|---|
| 7 | 2-(F$_3$C)pyridine | 2 | H | H | H | CH$_3$ | H | H | H | H | 0 | |
| 8 | 2-(F$_3$C)pyridine | 2 | H | H | H | Cl | Cl | CH$_3$ | CH$_3$ | H | 0 | |
| 9 | 2-Br-pyridine | 2 | H | H | H | H | H | H | H | H | 0 | 123–128 |
| 10 | 2-Br-pyridine | 2 | H | H | H | CH$_3$ | H | H | H | H | 0 | |
| 11 | 2-(H$_3$C)pyridine | 2 | H | H | H | H | H | H | H | H | 0 | 100–105 |
| 12 | 2-(H$_3$C)pyridine | 2 | H | H | H | CH$_3$ | H | H | H | H | 0 | |
| 13 | 2-(H$_5$C$_2$O)pyridine | 2 | H | H | H | H | H | H | H | H | 0 | |
| 14 | 2-(H$_5$C$_2$O)pyridine | 2 | H | H | H | CH$_3$ | H | H | H | H | 0 | |
| 15 | 2-(F$_3$C)pyridine | 2 | H | CH$_3$ | H | H | H | H | H | H | 0 | |
| 16 | 5-Cl-pyridine | 2 | H | H | H | H | H | H | H | H | 0 | 111–114 |
| 17 | 5-Cl-pyridine | 2 | H | H | H | CH$_3$ | H | H | H | H | 0 | |

TABLE 1-continued

Cyclopropanecarboxamides (I)

$$\text{A-O-} \bigcirc \text{(R}^1\text{)-O-CH(R}^2\text{)-(CH}_2)_n\text{-CH(R}^3\text{)-NH-C(=O)-C(R}^8\text{)}\begin{array}{c}\text{C(R}^4\text{)(R}^5\text{)}\\ \text{C(R}^6\text{)(R}^7\text{)}\end{array}$$

| Ex. No. | A | A attached in the ...-position | R¹ | R² | R³ | R⁴ | R⁵ | R⁶ | R⁷ | R⁸ | n | m.p. (°C.) or IR data (cm⁻¹) |
|---|---|---|---|---|---|---|---|---|---|---|---|---|
| 18 | 6-cyclopropyl-3-cyanopyridin-2-yl | 2 | H | H | H | H | H | H | H | H | 0 | |
| 19 | 6-cyclopropyl-3-cyanopyridin-2-yl | 2 | H | H | H | CH₃ | H | H | H | H | 0 | |
| 20 | 6-cyclopropyl-3-cyanopyridin-2-yl | 2 | H | CH₃ | H | H | H | H | H | H | 0 | |
| 21 | 6-cyclopropyl-3-cyanopyridin-2-yl | 2 | H | CH₃ | H | CH₃ | H | H | H | H | 0 | |
| 22 | pyrimidin-4-yl | 2 | H | H | H | H | H | H | H | H | 0 | 124 |
| 23 | pyrimidin-4-yl | 2 | H | H | H | CH₃ | H | H | H | H | 0 | 101 |
| 24 | pyrimidin-4-yl | 2 | H | CH₃ | H | H | H | H | H | H | 0 | 113 |
| 25 | pyrimidin-4-yl | 2 | H | CH₃ | H | CH₃ | H | H | H | H | 0 | 114–115 |
| 26 | 4-trifluoromethylpyrimidin-6-yl | 2 | H | H | H | H | H | H | H | H | 0 | |
| 27 | 4-trifluoromethylpyrimidin-6-yl | 2 | H | H | H | CH₃ | H | H | H | H | 0 | |

TABLE 1-continued

Cyclopropanecarboxamides

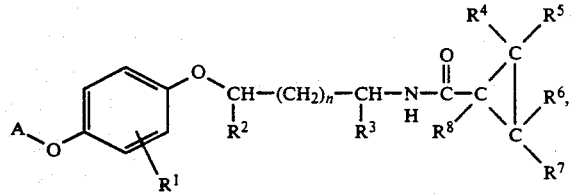

(I)

| Ex. No. | A | A attached in the ...-position | R¹ | R² | R³ | R⁴ | R⁵ | R⁶ | R⁷ | R⁸ | n | m.p. (°C.) or IR data (cm⁻¹) |
|---|---|---|---|---|---|---|---|---|---|---|---|---|
| 28 | 4-chloropyrimidin-2-yl | 2 | H | H | H | H | H | H | H | H | 0 | 103 |
| 29 | 4-chloropyrimidin-2-yl | 2 | H | H | H | CH₃ | H | H | H | H | 0 | 99–100 |
| 30 | 4-chloropyrimidin-2-yl | 2 | H | CH₃ | H | H | H | H | H | H | 0 | 143 |
| 31 | 4-chloropyrimidin-2-yl | 2 | H | CH₃ | H | CH₃ | H | H | H | H | 0 | |
| 32 | pyrimidin-5-yl | 5 | H | H | H | H | H | H | H | H | 0 | 98 |
| 33 | pyrimidin-5-yl | 5 | H | H | H | CH₃ | H | H | H | H | 0 | 99–100 |
| 34 | pyrimidin-5-yl | 5 | H | CH₃ | H | H | H | H | H | H | 0 | |
| 35 | 4-chloropyrimidin-5-yl | 5 | H | CH₃ | H | CH₃ | H | H | H | H | 0 | |
| 36 | 4-chloropyrimidin-4-yl | 4 | H | H | H | H | H | H | H | H | 0 | |
| 37 | 4-chloropyrimidin-4-yl | 4 | H | H | H | CH₃ | H | H | H | H | 0 | |
| 38 | pyrazin-2-yl | 2 | H | H | H | H | H | H | H | H | 0 | 121–126 |

TABLE 1-continued

Cyclopropanecarboxamides

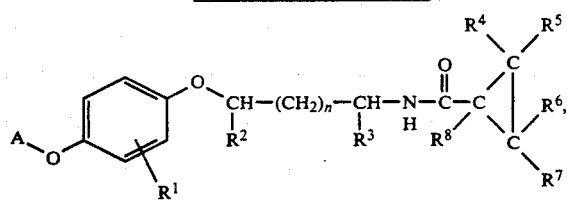

(I)

| Ex. No. | A | A attached in the ...-position | R¹ | R² | R³ | R⁴ | R⁵ | R⁶ | R⁷ | R⁸ | n | m.p. (°C.) or IR data (cm⁻¹) |
|---|---|---|---|---|---|---|---|---|---|---|---|---|
| 39 | pyrazine | 2 | H | H | H | CH₃ | H | H | H | H | 0 | 98–101 |
| 40 | pyridazine | 2 | H | CH₃ | H | H | H | H | H | H | 0 | 103–107 |
| 41 | 3,6-dimethylpyrazine | 2 | H | H | H | H | H | H | H | H | 0 | 108–112 |
| 42 | 3,6-dimethylpyrazine | 2 | H | H | H | CH₃ | H | H | H | H | 0 | 120–122 |
| 43 | 2,5-dimethylpyrazine | 2 | H | H | H | H | H | H | H | H | 0 | |
| 44 | 2,6-dimethylpyrazine | 2 | H | H | H | CH₃ | H | H | H | H | 0 | 90–94 |
| 45 | 3-methoxypyridazine | 3 | H | H | H | H | H | H | H | H | 0 | |
| 46 | 3-methoxypyridazine | 3 | H | H | H | CH₃ | H | H | H | H | 0 | |
| 47 | pyridine | 2 | H | H | H | H | H | H | H | H | 0 | 60–64 |
| 48 | 4,6-dimethylpyrimidine | 2 | H | H | H | H | H | H | H | H | 0 | 162 |

TABLE 1-continued

Cyclopropanecarboxamides

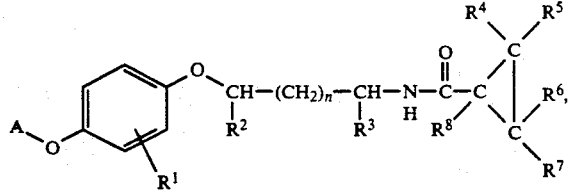

(I)

| Ex. No. | A | A attached in the ...-position | R¹ | R² | R³ | R⁴ | R⁵ | R⁶ | R⁷ | R⁸ | n | m.p. (°C.) or IR data (cm⁻¹) |
|---|---|---|---|---|---|---|---|---|---|---|---|---|
| 49 | (4,6-dimethylpyrimidin-2-yl, H₃C/CH₃ on pyrimidine with N,N) | 2 | H | H | H | CH₃ | H | H | H | H | 0 | 128 |
| 50 | (4,6-dimethoxypyrimidin-2-yl) | 2 | H | H | H | H | H | H | H | H | 0 | 137–138 |
| 51 | (3,6-dimethylpyrazin-2-yl) | 2 | H | CH₃ | H | H | H | H | H | H | 0 | 125–129 |
| 52 | (3,5-dimethylpyrazin-2-yl) | 2 | H | CH₃ | H | H | H | H | H | H | 0 | 112–115 |
| 53 | (pyrazin-2-yl) | 2 | H | CH₃ | H | CH₃ | H | H | H | H | 0 | 100–108 |
| 54 | (3,6-dimethylpyrazin-2-yl) | 2 | H | CH₃ | H | CH₃ | H | H | H | H | 0 | 82–86 |

USE EXAMPLE

In the following example, the pesticidal action of the compound of Example 1 according to the invention, or agents containing it, was compared with that of the closest art compound. The purity of compound no. 1 and of comparative agent A was >95%.

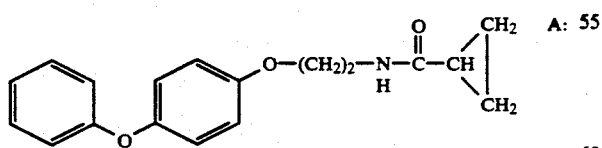

A:

disclosed in EP-A-258,733 Example 2

The concentrations at which the candidate compounds exhibit 100% kill or inhibition are the minimum concentrations. At least two experiments are run for each concentration and an average is formed.

Example A

*Dysdercus intermedius* (Cotton Stainer); Ovicidal Action

The experiment was carried out in 1 liter jars containing 200 g of sterile quartz sand (particle size 0–3 mm). Prior to the experiment, 20 ml of the aqueous active ingredient formulations was poured onto this sand. Ten larvae of the fourth stage were then introduced into each jar. The food proffered was swollen cottonseed, which was changed once a week. The sand was also moistened once a week with pure water. The temperature was kept at 25° to 27° C. The observation period extended to molting to the adult. A sample was considered to be effective when, at the end of the experiment, the animals were either dead or exhibited considerable morphological defects, or giant larvae or adultoids had formed.

The results are given in Table A.

TABLE A

| Compound No. | Active ingredient conc. [ppm] | Mortality (%) |
| --- | --- | --- |
| 1 | 0.1 | 100 |
| A | 1 | 100 |

We claim:

1. A cyclopropanecarboxamide of formula (I)

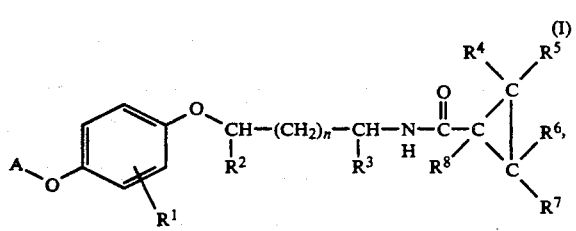

wherein:

$R^1$ is hydrogen, halogen or $C_1$–$C_3$-alkyl;

$R^2$ and $R^3$ are each independently hydrogen or $C_1$–$C_4$-alkyl;

$R^4$ to $R^8$ are each independently hydrogen, halogen, or $C_1$–$C_4$-alkyl;

A is a hetaryl radical which is one member selected from the group consisting of pyrid-2-yl, pyrid-3-yl, and pyrid-4-yl, wherein said hetaryl radical is either unsubstituted or substituted by a group $R^9$ which is hydrogen, halogen, $C_1$–$C_4$-alkyl, $C_1$–$C_3$-haloalkyl, $C_1$–$C_4$-alkoxy, $C_1$–$C_3$-haloalkoxy, $C_3$–$C_6$-cycloalkyl, cyano, or nitro; and n is 0 or 1.

2. The cyclopropanecarboxamide of claim 1, wherein said hetaryl radical is substituted by 1 to 4 groups $R^9$.

3. The cyclopropanecarboxamide of claim 2, wherein $R^9$ is fluorine, chlorine, bromine, methyl, ethyl, propyl, butyl, isopropyl, isobutyl, sec-butyl, $C_1$–$C_3$-fluoroalkyl, $C_1$–$C_3$-chloroalkyl, methoxy, ethoxy, propoxy, butoxy, $C_1$–$C_3$-fluoroalkoxy, $C_1$–$C_3$-chloroalkoxy, cyclopropyl, cyclobutyl, cyclopentyl, or cyclohexyl.

4. The cyclopropanecarboxamide of claim 2, wherein $R^9$ is fluorine, chlorine, methyl, ethyl, fluoromethyl, difluoromethyl, trifluoromethyl, pentafluoroethyl, 2,2,2-trifluoroethyl, trichloromethyl, 2,2,2-trichloroethyl, methoxy, ethoxy, isopropoxy, trifluoromethoxy, 1,1,2,2-tetrafluoroethoxy, pentafluoroethoxy, trichloromethoxy, or cyclopropyl.

5. The cyclopropanecarboxamide of claim 1, wherein $R^1$, $R^3$ and $R^8$ are hydrogen, $R^2$ is hydrogen or methyl, $R^4$ to $R^7$ are each independently hydrogen, chlorine, fluorine, or $C_1$–$C_4$-alkyl, and n is 0.

6. A pesticide containing, together with a conventional carrier, a pesticidally effective amount of a cyclopropanecarboxamide of formula (I)

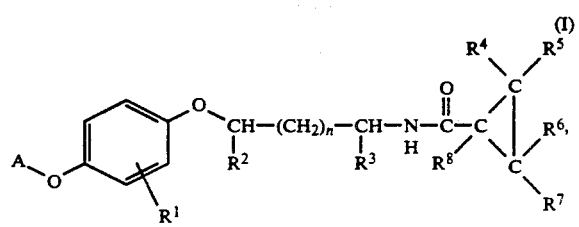

wherein:

$R^1$ is hydrogen, halogen or $C_1$–$C_3$-alkyl;

$R^2$ and $R^3$ are each independently hydrogen or $C_1$–$C_4$-alkyl;

$R^4$ to $R^8$ are each independently hydrogen, halogen, or $C_1$–$C_4$-alkyl;

A is a hetaryl radical which is one member selected from the group consisting of pyrid-2-yl, pyrid-3-yl, and pyrid-4-yl, wherein said hetaryl radical is either unsubstituted or substituted by a group $R^9$ which is hydrogen, halogen, $C_1$–$C_4$-alkyl, $C_1$–$C_3$-haloalkyl, $C_1$–$C_4$-alkoxy, $C_1$–$C_3$-haloalkoxy, $C_3$–$C_6$-cycloakyl, cyano, or nitro; and n is 0 or 1.

7. The pesticide of claim 6, wherein said hetaryl radical substituted by 1 to 4 groups $R^9$.

8. The pesticide of claim 7, wherein $R^9$ is fluorine, chlorine, bromine, methyl, ethyl, propyl, butyl, isopropyl, isobutyl, sec-butyl, $C_1$–$C_3$-fluoroalkyl, $C_1$–$C_3$-chloroalkyl, methoxy, ethoxy, propoxy, butoxy, $C_1$–$C_3$-fluoroalkoxy, $C_1$–$C_3$-chloroalkoxy, cyclopropyl, cyclobutyl, cyclopentyl or cyclohexyl.

9. The pesticide of claim 7, wherein $R^9$ is fluorine, chlorine, methyl, ethyl, fluoromethyl, difluoromethyl, trifluoromethyl, pentafluoroethyl, 2,2,2-trifluoroethyl, trichloromethyl, 2,2,2-trichloroethyl, methoxy, ethoxy, isopropoxy, trifluoromethoxy, 1,1,2,2-tetrafluoroethoxy, pentafluoroethoxy, trichloromethoxy, or cyclopropyl.

10. The pesticide of claim 6, wherein $R^1$, $R^3$ and $R^8$ are hydrogen, $R^2$ is hydrogen or methyl, $R^4$ to $R^7$ are each independently hydrogen, chlorine, fluorine or $C_1$–$C_4$-alkyl, and n is 0.

11. A process for combating a pest from the class of insects, mites and nematodes, comprising administering to said pest or to the habitat of said pest a pesticidally effective amount of a cyclopropanecarboxamide of formula (I)

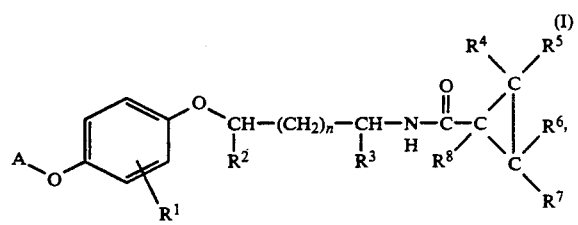

wherein:

$R^1$ is hydrogen, halogen or $C_1$–$C_3$-alkyl;

$R^2$ and $R^3$ are each independently hydrogen or $C_1$–$C_4$-alkyl;

$R^4$ to $R^8$ are each independently hydrogen, halogen, or $C_1$–$C_4$-alkyl;

A is a hetaryl radical which is one member selected from the group consisting of pyrid-2-yl, pyrid-3-yl, and pyrid-4-yl, wherein said hetaryl radical is either unsubstituted or substituted by a group $R^9$ which is hydrogen, halogen, $C_1$–$C_4$-alkyl, $C_1$–$C_3$-haloalkyl, $C_1$–$C_4$-alkoxy, $C_1$–$C_3$-haloalkoxy, $C_3$–$C_6$-cycloalkyl, cyano, or nitro; and n is 0 or 1.

12. The process of claim 11, wherein said hetaryl radical substituted by 1 to 4 groups $R^9$.

13. The process of claim 12, wherein $R^9$ is fluorine, chlorine, bromine, methyl, ethyl, propyl, butyl, isopropyl, isobutyl, sec-butyl, $C_1$–$C_3$-fluoroalkyl, $C_1$–$C_3$-chloroalkyl, methoxy, ethoxy, propoxy, butoxy, $C_1$–$C_3$- fluoroalkoxy, $C_1$–$C_3$-chloroalkoxy, cyclopropyl, cyclobutyl, cyclopentyl or cyclohexyl.

14. The process of claim 12, wherein $R^9$ is fluorine, chlorine, methyl, ethyl, fluoromethyl, difluoromethyl, trifluoromethyl, pentafluoroethyl, 2,2,2-trifluoroethyl, trichloromethyl, 2,2,2-trichloroethyl, methoxy, ethoxy, isopropoxy, trifluoromethoxy, 1,1,2,2-tetrafluoroethoxy, pentafluoroethoxy, trichloromethoxy, or cyclopropyl.

15. The process of claim 11, wherein $R^1$, $R^3$ and $R^8$ are hydrogen, $R^2$ is hydrogen or methyl, $R^4$ to $R^7$ are each independently hydrogen, chlorine, fluorine or $C_1$–$C_4$-alkyl, and n is 0.

* * * * *